(12) United States Patent
Kostka et al.

(10) Patent No.: US 9,891,168 B2
(45) Date of Patent: Feb. 13, 2018

(54) DEVICE AND METHOD FOR SENSING AT LEAST ONE PARTIALLY SPECULAR SURFACE WITH COLUMN-BY-COLUMN ANALYSIS OF THE GLOBAL OR LOCAL INTENSITY MAXIMUM

(71) Applicant: Fraunhofer-Gesellschaft zur Foerderung der angewandten Forschung e.V., Munich (DE)

(72) Inventors: Guenther Kostka, Erlangen (DE); Peter Schmitt, Erlangen (DE); Christian Huegel, Wendelstein (DE); Lars Seifert, Neumarkt (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 135 days.

(21) Appl. No.: 15/048,767

(22) Filed: Feb. 19, 2016

(65) Prior Publication Data

US 2016/0169798 A1 Jun. 16, 2016

Related U.S. Application Data

(63) Continuation of application No. PCT/EP2014/067733, filed on Aug. 20, 2014.

(30) Foreign Application Priority Data

Aug. 21, 2013 (DE) ............ 10 2013 216566

(51) Int. Cl.
*G01N 21/57* (2006.01)
*G01N 21/88* (2006.01)
*G01B 11/25* (2006.01)

(52) U.S. Cl.
CPC ......... *G01N 21/57* (2013.01); *G01B 11/2518* (2013.01); *G01N 21/8806* (2013.01); *G01N 2201/061* (2013.01); *G01N 2201/08* (2013.01)

(58) Field of Classification Search
CPC ............ G01N 21/57; G01N 21/8806; G01N 2201/08; G01N 2201/061; G01B 11/2518
See application file for complete search history.

(56) References Cited

U.S. PATENT DOCUMENTS 3,439,988 A * 4/1969 Breske ............... G01N 21/8803
  353/122
4,629,319 A * 12/1986 Clarke ............... G01N 21/88
  356/237.2

(Continued)

FOREIGN PATENT DOCUMENTS

DE 19821059 A1 12/1999
DE 19944354 A1 4/2001

(Continued)

OTHER PUBLICATIONS

Werling, Stefan B., "Deflektometrie zur automatischen Sichtpruefung und Reconstruktion spiegelnder Oberflaechen", KIT Scientific Publishing, Karlsruhe, Germany, vol. 3, Translation of Title: Deflectometry for Automatic Visual Inspection and Reconstruction of Reflecting Surfaces, Jan. 2011, pp. 128-135.

*Primary Examiner* — Michael P Lapage
(74) *Attorney, Agent, or Firm* — Michael A. Glenn; Perkins Coie LLP (57) ABSTRACT

Among a device and a method for sensing at least partially specular surfaces, the device includes a detection face and an illuminator configured to project a pattern onto the detection face by reflection via the at least partially specular surface.

22 Claims, 5 Drawing Sheets

(56) References Cited

U.S. PATENT DOCUMENTS

| | | | |
|---|---|---|---|
| 4,853,777 A * | 8/1989 | Hupp | G01B 11/303 348/128 |
| 5,122,672 A * | 6/1992 | Mansour | G01B 11/303 250/559.01 |
| 5,153,844 A * | 10/1992 | Beni | G01B 11/306 356/237.2 |
| 5,225,890 A | 7/1993 | Lee et al. | |
| 5,887,077 A * | 3/1999 | Bongardt | G01J 3/50 382/149 |
| 6,100,990 A * | 8/2000 | Ladewski | G01N 21/55 356/124 |
| 7,532,333 B2 | 5/2009 | Haeusler et al. | |
| 7,639,349 B2 | 12/2009 | Ersue et al. | |
| 7,843,574 B2 | 11/2010 | Schmitt et al. | |
| 2005/0238237 A1 | 10/2005 | Haeusler et al. | |
| 2008/0273211 A1 | 11/2008 | Schmitt et al. | |
| 2009/0316113 A1 | 12/2009 | Ernst et al. | |
| 2011/0193954 A1 | 8/2011 | Walecki et al. | |
| 2012/0207380 A1 * | 8/2012 | Le Moal | G01B 11/25 382/141 |

FOREIGN PATENT DOCUMENTS

| | | |
|---|---|---|
| DE | 10127304 A1 | 12/2002 |
| DE | 102004007828 A1 | 9/2005 |
| DE | 102004020419 B3 | 10/2005 |
| DE | 102005044912 A1 | 4/2007 |
| DE | 102005058873 A1 | 6/2007 |
| DE | 102006030273 A1 | 1/2008 |
| DE | 102010015566 A1 | 10/2011 |
| DE | 102012100281 A1 | 7/2013 |
| EP | 1837623 A1 | 9/2007 |
| EP | 1882896 A1 | 1/2008 |
| EP | 1925908 A1 | 5/2008 |
| EP | 1995083 A1 | 11/2008 |
| WO | 0123833 A1 | 4/2001 |

* cited by examiner

DEVICE AND METHOD FOR SENSING AT LEAST ONE PARTIALLY SPECULAR SURFACE WITH COLUMN-BY-COLUMN ANALYSIS OF THE GLOBAL OR LOCAL INTENSITY MAXIMUM

CROSS-REFERENCE TO RELATED APPLICATIONS

This application is a continuation of copending International Application No. PCT/EP2014/067733, filed Aug. 20, 2014, which claims priority from German Application No. 102013216566.8, filed Aug. 21, 2013, which are each incorporated herein in its entirety by this reference thereto.

The present invention relates to a device for sensing at least partially specular surfaces and to a method of sensing same.

BACKGROUND OF THE INVENTION

For economic reasons, mainly contactless measuring methods are employed for inspecting glossy or high-gloss surfaces such as those of alloy wheels, for example, for surface defects such as dents, bumps, drops or bumps of lacquer (paint), scratches or grooves, for example. In the functional field of industry, surface defects are typically sensed and detected by means of optical capturing methods.

With sufficiently cooperative, i.e., diffusely scattering, surfaces, shape measurement may also be affected by means of optical scanning, for example by means of optical triangulation methods. By means of optical triangulation methods such as a laser light-slit method, for example, surfaces comprising a sufficiently large diffuse scattering contribution can be sensed and measured. Said methods are not suitable in most cases for surfaces having a large or a very large amount of gloss. In addition, they exhibit a limited spatial resolution and are not, or hardly, sensitive to small local differences in inclination of the surfaces as occur on above-mentioned surface defects of alloy wheels, for example.

Quality control with regard to surface defects of specular surfaces such as on alloy rims, for example lacquer defects, casting defects, mechanical damages or inclusions within the material, so far has mostly been performed by means of a visual examination on the part of human examiners for lack of alternative test procedures. Said visual examination may be very time-consuming and/or costly. In addition, such visual examination is subjective and may not be reproducible and/or quantifiable in a reliable manner. Fatigue or fluctuations in the ability to concentrate on the part of the human examiner may give rise to the risk of defect slippage.

Said surface defects are visible to the human observer due to a local variation of the reflected ambient light. Small or very small lacquer defects which have a small height extension, for example within the micrometer range, may possibly not be reliably sensed by means of the laser light-slit method. Deflectometry methods are suited to sense especially highly reflecting surfaces with regard to their shapes, the local angles of inclination and surface defects, and/or to measure the shape of the surface. Typically, a sequence of bright and dark strips is produced on an extensive light source, e.g., a fluorescent screen, and sequentially mapped (projected, imaged) in reflection via the specular surface by means of an area scan camera. The course of the striped pattern within the sequentially taken cameral pictures depends on the local and global shape, i.e., on the position and inclination, of the surface and may be evaluated automatically, i.e., by means of a computer program, from the sequence of pictures taken. On the condition that the arrangement of the camera, the object (surface) and the light source is calibrated, the three-dimensional shape of the surface may be reconstructed in the course of the evaluation. An evaluation of local shape deviations may possibly also be achieved without a fully calibrated setup and/or reconstruction algorithm.

In the deflectometry method, a sequence of pictures may be taken, via an area scan camera, for each surface area to be captured; the relative position between the camera, the surface and the fluorescent screen normally may not change during a capturing process, i.e., relative motion may not take place. In addition, in this method the camera pictures that have been captured and are to be evaluated may be transmitted, for data processing, to an evaluating unit, for example an evaluation calculator. The data transmission rate for transmitting two-dimensional camera pictures to a computer is currently limited, for technical reasons, to a maximum of 100 pictures/s, so that the object is typically moved discontinuously and so that a reduced testing throughput is achieved. The useful step-wise positioning of the object, or of the surface, in relation to the metrological arrangement of the camera and the fluorescent or projection screen (or vice versa, of the metrological arrangement in relation to the object) may additionally involve a large amount of effort, i.e., may be costly and/or relatively slow, with regard to the mechanical components that may be used such as with regard to the axes of displacement that are to be realized.

For automatically detecting surface defects that are very small in terms of their surface areas or heights, a correspondingly high pixel resolution of the camera and a correspondingly finely resolved striped pattern may be used. On account of the sampling theorem it may be useful for a lateral extension of the pattern, i.e. a stripe width of the extension, to correspond to or fall below the extension of the defects to be detected.

DE 102004007828 A1 describes an optical method of sensing surfaces of three-dimensional bodies wherein the surface, the illuminating means and the camera may be made to have at least one defined geometric relation, for the period of the respective picture taking, by means of movement means, so as to achieve a constant capturing quality for each area to be inspected and a high recognition rate for defects. During the exposure and/or picture-taking time of the camera, relative motion between the camera, the surface and the illuminating means may not take place. This means that the entire surface may be sensed step-by-step, i.e. one surface region after the other, whereby a reduced testing throughput is achieved since the arrangement of the surface, the camera and the illumination may be repositioned in each case between the individual picture taking operations.

SUMMARY

According to an embodiment, a device for sensing at least partially specular surfaces may have: a detection face; illuminator configured to project a pattern onto the detection face by reflection via the at least partially specular surface; and a sensing unit configured to sense the pattern projected onto the detection face and to evaluate an image, which has been sensed from the detection face, in a column-by-column manner in terms of a global intensity maximum; the illuminator including a line projector configured to emit a line pattern, the line pattern being a light fan beam.

According to another embodiment, a measurement system may have at least one device for sensing at least partially specular surfaces in accordance with claim 1, the measurement system being configured to measure an object to be measured which includes a surface to be sensed.

According to another embodiment, a method of sensing at least partially specular surfaces may have the steps of: arranging a detection face; projecting, by means of an illuminator, a pattern onto the detection face by reflection via the at least partially specular surface; sensing the pattern projected onto the detection face; evaluating an image, which has been sensed by the detection face, with regard to a global intensity maximum in a column-by-column manner; said projecting being implemented such that a line pattern that is a light fan beam is emitted.

According to another embodiment, a non-transitory digital storage medium may have a computer program stored thereon to perform the inventive method when said computer program is run by a computer.

The core idea of the present invention consists in having found that the above object can be achieved in that a detectable or evaluable image of a pattern can be produced on the detection face by projecting the pattern onto a detection face by reflection via the at least partially specular surface, so that the image of the pattern on the detection face enables conclusions to be drawn in terms of surface defects.

In accordance with an embodiment, an illuminating means projects a pattern in the direction of an at least partially specular surface reflecting the pattern, so that the pattern is projected onto a detection face. A sensing unit is configured to sense the pattern projected onto the detection face.

What is advantageous about this embodiment is that a surface defect of the at least partially specular surface may be recognized in that an inclination angle of the surface that is altered by the surface defect may result in an altered projection of the pattern on the detection face, that said alteration can be ascertained and the surface defect can thus be detected. Moreover, visual examination may be supplemented by automatic inspection and be performed in a continuous form so that step-by-step positioning of the measuring devices or of the surface to be tested may be dispensed with.

In accordance with an alternative embodiment, the illuminating unit emits ultraviolet or extreme ultraviolet light which is shifted, by phosphorescent or fluorescent properties of the detection face, to a visible range on the detection face to which cameras are more sensitive. What is advantageous about this embodiment is that due to the use of ultraviolet or extreme ultraviolet illumination, a short wavelength of the illumination can be exploited for high resolution with regard to the surface defects on the surface examined.

BRIEF DESCRIPTION OF THE DRAWINGS

Embodiments of the present invention will be detailed subsequently referring to the appended drawings, in which.

DETAILED DESCRIPTION OF THE INVENTION

Before embodiments of the present invention will be explained in detail below with reference to the figures, it shall be noted that elements, objects and/or structures that are identical, identical in function or identical in effect are provided with the same reference numerals in the different figures, so that the descriptions of said elements that are presented in different embodiments are interchangeable and/or mutually applicable.

Figure 1A:
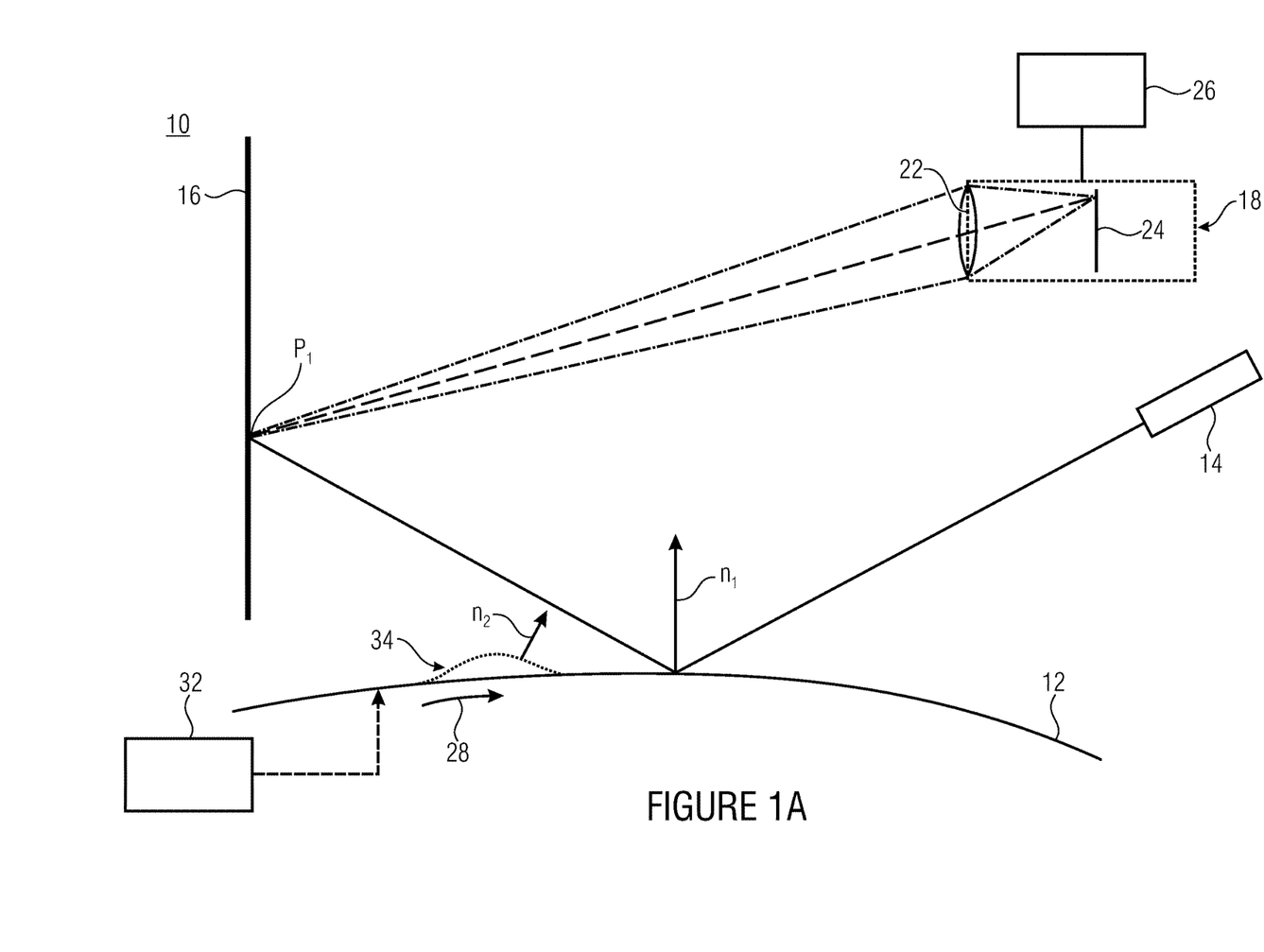
FIG. 1a shows a device for sensing an at least partially specular surface.

FIG. 1a shows a device 10 for sensing an at least partially specular surface 12. The at least partially specular surface 12 may be a surface of an alloy rim for car wheels or the like, a lacquered metal sheet or a mirror surface. A lacquered metal sheet may be a gloss-lacquered, transparently lacquered, metallically specular metal sheet. The at least partially specular surface may alternatively be a ceramic or glass surface that is to be measured and/or examined. Alternatively, the device 10 enables, e.g., eye glasses or other shiny technical surfaces to be measured.

Even if the explanations which follow relate to partially specular surfaces 12 of alloy wheels, said explanations shall also apply, unless illustrated otherwise, to other at least partially specular surfaces such as the ones just mentioned above, for example.

An illuminating means 14 is configured to project a pattern such as a point of light, one or several lines, a striped pattern or any other pattern, for example, onto a detection face 16 by reflection at the at least partially specular surface 12. A position or an area $P_1$ at which the pattern is projected onto the detection face in this context is dependent on a local surface inclination with a surface normal $n_1$ and an irradiation angle between the illuminating means 14 and the surface normal $n_1$. The pattern may be projected by using light, in particular laser light. What is advantageous about a pattern projected by using laser is that an increased depth-of-focus range of the laser may be exploited on account of a larger Rayleigh length of the laser, for example as compared to collimated light of a projection lamp. Alternatively or additionally, the illuminating means 14 may be configured to emit short-wave or particularly short-wave radiation such as ultraviolet (UV) or extreme ultraviolet (XUV) light so as to achieve particularly highly resolved scanning of the at least partially specular surface 12. Highly focused UV or XUV radiation enables highly resolved surface scanning on the basis of the shorter wavelength.

What is advantageous about this embodiment is that a surface defect on an at least partially specular surface may possibly be sensed indirectly by means of a magnification function at the detection plane. Influences that are due to reflections on the at least partially specular surface 12 and that possibly disturb sensing may thus be reduced. Simultaneously, light having a shorter wavelength may be employed for projecting the pattern onto the detection face 12, so that surface defects having small spatial extensions will be detectable.

The illuminating means 14 may be a line projector, for example, in particular a laser line projector which projects a light fan beam onto the detection face 16. The pattern may be formed of light, in particular laser light, which comprises visible wavelengths. Alternatively or additionally, the light projecting the pattern may also comprise other wavelengths, for example ultraviolet (UV) or extreme ultraviolet (XUV)

light, for example. The UV or XUV light may be converted to visible light or long-wave radiation on or at the detection face, for example by phosphorescent or fluorescent substances or materials. A UV or XUV light that has been converted to visible light and is scattered by the detection face 16 may be sensed by conventional silicon-based camera sensors. Alternatively or additionally, it is possible to employ different wavelengths for a further or the same testing operation, for example so as to sense different depth or test ranges of the at least partially specular surface 12.

The detection plane 16 may be, e.g., a diffusely scattering non-transparent scattering foil which is sensed by a sensing unit 18 from a direction, from which the pattern is projected onto the detection face 16 (side of incidence), via conventional imaging optics 22 of the sensing unit 18 and/or a detector face of an electronic area scan camera. Alternatively, the detection face 16 may also be at least partially transparent such as a semi-transparent scattering foil, for example, so that the pattern can be sensed from a side of the detection face 16 which faces away from the side of incidence. Thus, for example, a pattern projected onto the detection face 16 by a UV or XUV laser can be converted to visible light by phosphorescent or fluorescent substances at the detection face 16 and may be scattered, so that the pattern on the side facing away from the side of incidence will be visible and, thus, can be sensed by the sensing unit 18 when the latter is arranged to sense that side of the detection face 16 which faces away from the side of incidence.

The sensing unit 18 such as an area scan or line scan camera, for example an electronic camera, is configured to sense the detection face 16, for example in that the sensing unit 18 captures a continuous or discontinuous sequence of pictures of the pattern projected onto the detection face 16. The sensing unit 18 comprises imaging optics 22 and a detector face, such as a camera chip or any other image sensor 24, the imaging optics 22 being configured to compensate for a varying distance between the at least partially specular surface 12, the illuminating means 14 and/or the detection face 16 in such a manner that a focused image of the pattern can be mapped onto the image sensor 24. The image sensor (camera chip) 24 may comprise one or several, e.g. silicon-based sensors, in particular if the pattern is scattered at the detection face 16 in the form of light of a visible wavelength This may be effected by projecting the pattern with UV or XUV light and by converting the UV or XUV light to a visible range.

The sensing unit 18 may be a 3D measuring camera such as a light-slit camera, for example. These may achieve measurement rates of more than ten thousand profile measurements per second. By means of sequential, high-frequency measurement of the pattern on the detection face during a relative motion 28 between the measurement arrangement, i.e. the illuminating means 14 and the detection face 16 as well as the sensing unit 18, and the at least partially specular surface 12 it is possible to sequentially achieve partial or complete sensing of the at least partially specular surface 12. A light-slit measuring camera may enable fast determination of the position of a light line pattern and/or of the position of a light line on the detection face 16 by the light-slit measuring camera so that a data reduction may be performed on the image sensor 24 or within the sensing unit 18. To this end, the sensing unit 18 may include a local evaluating unit configured to evaluate, for example, the sensed image column by column with regard to a local or global intensity maximum and to output the corresponding line value(s) of the local or global maximum as a scalar. In particular, such a determination of the position enables a first data reduction and, consequently, faster transmission of individual pictures to the evaluating unit 26 since only the extracted positional information is transmitted instead of complete pictures. In addition, a series of additional information such as an intensity of the evaluated light line per measuring point or a line width per measuring point may be provided. This additional information or data may be evaluated by additional evaluation steps. For example, the existence of a defect may be inferred from a change, which is high in frequency in the position space, of a brightness or of the line width in combination with the evaluation of the progression of positions of the line. For example, the absence of at least parts of the pattern within a certain area of the detection face 16 may point to a defect. For example, if a continuous curvature is expected, at the at least partially specular surface 12, between two mutually inclined portions of the at least partially specular surface 12, said continuous curvature may result in that the pattern traverses a specific area at the detection face 16 on account of the curvature. If the component comprises a defect, for example a bend-shaped transition, between said mutually inclined portions, the pattern will possibly be abruptly shifted from one area (sensing of the first portion of the at least partially specular surface 12) to a different area (sensing the second portion inclined in relation to the first area), so that the pattern is not present between said two areas of the detection face 16. In principle, a change in the pattern, for example when a constant pattern is expected at the detection face 16, or a non-change of the pattern, for example when a curvature of a projected line of the pattern is expected, may enable conclusions to be drawn that there is a surface defect.

A focus of the sensing unit 18 to the detection face 16 and/or the pattern is adjustable on the basis of a variable distance between the illuminating means and the at least partially specular surface 12.

Depending on the respective implementation, the sensing unit 18 can sense image data or light line position measurement data. An evaluation of raw measurement data may be performed on an evaluating unit 26 such as a measuring computer, e.g. by means of specifically implemented computer programs which may possibly be employed for standard picture processing operations or even specifically developed algorithms for automatic detection of defect structures caused by surface defects or for measuring the at least partially specular surface 12. Detection of defects such as the surface defect 34 may be performed on the basis of a distinction between long-range, i.e. large-area, defect-free target structures and short-range, i.e. small-area, defective structures. Such a distinction may be made, for example, by means of specific spatial-frequency filtering and corresponding discrimination within the spatial-frequency space. The distinction between defect-free and defective structures may also be performed, alternatively or additionally, by means of linear or non-linear filter operations within the position space. The evaluating means 26 may be configured to receive a sequence of single-profile data from the sensing means 18 and to assemble them to form an overall representation of the sensed surface. This may enable determining local defect zones by means of local differences in inclination. Moreover, generation of the overall representation enables calibrating and reconstructing the entire surface by integrating the surface inclination, and enables measuring the surface.

The use of filters within the position space may enable taking into account data domains containing object boundaries (such as edges or bends). To this end, a respective filter setting may be adapted to a respective alignment of the object boundary, so that defective or artefact-fraught evaluation of data, for example by the measuring computer 26, at said object boundaries can be avoided. For example, object boundaries in an alloy rim may be edges between treads and side faces or edges of the side face that are formed by spokes of the alloy rims.

The illuminating means 14 projects the pattern onto the at least partially specular surface 12. The specularly, i.e. mirroringly, reflected pattern and/or light is projected onto the detection face 16, where it is at least partially diffusely reflected or scattered, so that the pattern can be mapped to the image sensor 24 via the imaging optics 22 from the sensing unit 18, and so that the position of the pattern may be evaluated on the image sensor 24, for example in a column-by-column manner.

Information received in this manner about the position $P_1$ of the pattern on the detection face 16 may be conveyed or provided to an evaluating means 26, e.g. in the form of a profile-like progression of positions.

The evaluating means 26 may be a measuring computer, for example, that is configured to collect received or provided positional information and/or positional profiles over a period of time. By means of a successive or sequential series of a plurality or multitude of such positional profiles, for example while the at least partially specular surface 12 undergoes a relative motion 28 in relation to the metrological components, the illuminating means 14, the detection face 16 and/or the sensing unit 18, the evaluating means 26 may merge the successive or sequential positional profiles to form a two- or three-dimensional virtual image or reconstruction, so that a comparison between the virtual image or the reconstruction and a defect-free target structure is possible.

The relative motion 28 may be achieved, for example, by a positioning unit 32, such as a rotating unit for subjecting the alloy rim to a rotation, so that the alloy rim and, consequently, the at least partially specular surface 12 rotates before the illuminating means 14 and so that different portions of the at least partially specular surface 12 reflect the pattern. A rotational movement may be advantageous in particular with radially symmetrical surfaces so as to enable speedy evaluation. By means of the relative motion 28 between the at least partially specular surface 12 to be inspected and the metrological components, illuminating means 14, detection face 16 and/or sensing unit 18, the information of a surface zone, i.e. of a part of or the entire at least partially reflecting surface 12, can be collected and composed and evaluated and/or measured in terms of surface defects 34, for example within the evaluating means 26.

Due to the dependence of the position $P_1$ on the angle of incidence of the illuminating means 14 onto the at least partially specular surface 12, the relative motion 28 may also be described as a shift in the illuminating means 14 in relation to the at least partially specular surface 12 (or vice versa). A limitation or avoidance of a relative motion between the illuminating means 14 and/or the detection face 16 may avoid a projection of the pattern outside the detection face or a shift of the detection plane 16 outside sensing area of the sensing means 18.

The surface defect 34 may be a lacquer defect, a casting defect, mechanical damages such as a bump, inclusions within the material, lacquer bumps or lacquer drops, varying lacquer layer thicknesses, a radial or lateral runout, scratches or grooves, for example. Generally, other surface defects comprising varying surface normals n on the at least partially specular surface may also be detected.

The surface defect 34 comprises a surface normal $n_2$ different from $n_1$. Due to the different surface normals $n_1$ and $n_2$, the presence of the surface defect 34 in that area of the at least partially specular surface 12 which reflects the pattern may result in a change in the position at which the pattern is projected. This change in the location can be sensed by the sensing unit 18.

For a high lateral detail resolution of the measurement it may be advantageous to employ as highly focused a laser line projector as possible as the illuminating means 14. In the event of a relevant or intense variation of a height profile of the at least partially specular surface 12 it may also be advantageous to employ a laser line projector having a particularly large Rayleigh length, i.e. a particularly large depth-of-focus range of the laser. Embodiments show laser line projectors having a Rayleigh length that is larger than a distance between the illuminating means 14, the at least partially specular surface 12 and the detection face 16. Alternative embodiments show laser line projectors comprising 0.5 times, double, five times or ten times this distance as the Rayleigh length.

Embodiments show illuminating means employing automatic focusing of the respective illumination, e.g. that of a laser, so as to sense as large an object area as possible with as good, i.e. exact, a focusing as possible, such as laser focusing. Said automatic focusing may be controlled on the basis of a distance between the at least partially specular surface 12, the illuminating means 14, the detection face 16 and the sensing unit 18, for example by a motorized controller implementing an auto focus. Focusing means, in particular laser focusing means, may be employed for increasing the depth-of-focus range of the pattern on the surface.

Figure 1B:
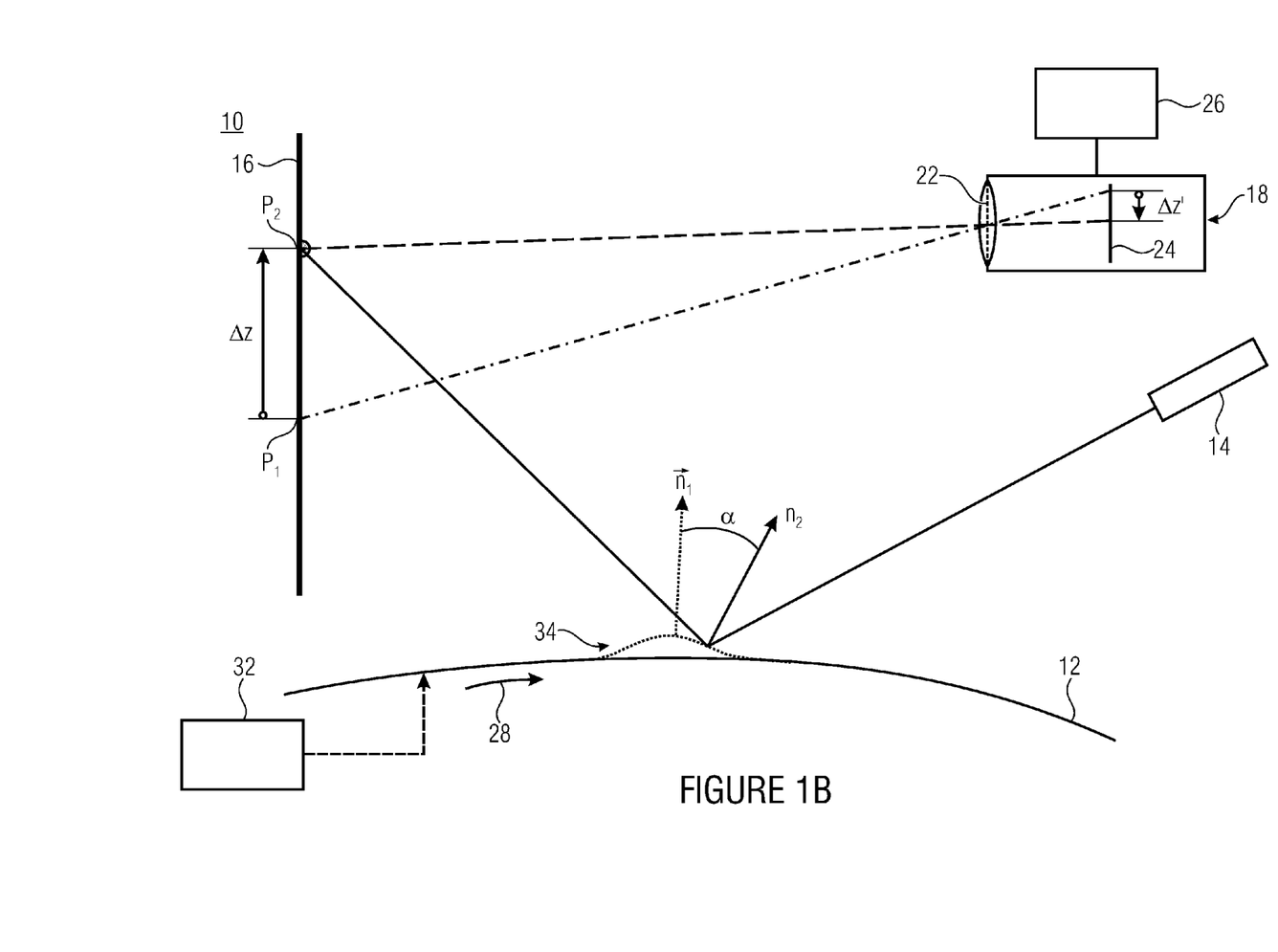
FIG. 1b shows the device of FIG. 1a, wherein a surface defect is detected on the at least partially specular surface.

FIG. 1b shows a device 10 wherein the surface defect 34 is detected on the at least partially specular surface 12. The pattern of the illuminating means 14 is projected onto the detection face 16 by reflection at the at least partially specular surface 12 and of the surface defect 34. The surface defect 34 comprises the surface normal $n_2$, so that the surface normals $n_1$ and $n_2$ comprise an angle $\alpha$ in relation to each other. On account of the surface normal $n_2$ being inclined in relation to the surface normal $n_1$ by the angle $\alpha$, the pattern of the illuminating means 14 is reflected at a different angle at the surface defect 34 than at the at least partially specular surface 12 in FIG. 1a. Said reflection of the pattern at a modified angle results in a projection of the pattern at the detection face 16 at a location $P_2$, which has a distance $\Delta z$ in relation to the location $P_1$. The distance $\Delta z$ is, inter alia, dependent on the angle $\alpha$, so that an extent of the shift and/or of the distance $\Delta z$ between the locations $P_1$ and $P_2$ may enable conclusions to be drawn in terms of a type and an extent of the surface defect 34. The shift $\Delta z$ may be sensed by the sensing unit 18 as a changed pattern at the detection face 16. Depending on an optical adjustment of the sensing unit 18, for example a distance of the image sensor 24 to the detection face 16 and/or a refractive index of the imaging optics 22, the distance $\Delta z$ on the image sensor 24 is mapped as a distance $\Delta z'$. A comparison of individual pictures of the pattern can be performed in the evaluating means 26, and the surface defect 34 can be ascertained. If the evaluating means 26 is supplied with information, such as advancement, of the positioning means 28 and/or of the object having the at least partially specular surface 12, an image of the object and indications concerning the type, location and extension of surface defects may possibly be produced at the evaluating means 26. Alternatively or additionally, the pattern may be deformed by the surface defect 34, for example when the pattern comprises, on the at least partially specular surface 12, a larger extension in one or several directions than does the surface defect 34. In such a case, e.g. parts of the pattern that are reflected at the surface defect 34 may be shifted at the detection face 16 in relation to parts of the pattern which are reflected at the at least partially specular surface 12, so that a deformed or distorted pattern can be detected at the detection face 16.

A relationship between the angle α and the distance Δz may be adjustable as a function of an angle at which the illuminating means 14 is arranged in relation to the surface normal $n_1$ and/or of a distance between a location of the reflection at the at least partially specular surface 12 and the detection face. If the pattern is a laser pattern, for example, in particular with a laser having a large Rayleigh length, the device 10 allows mapping of the surface defect 34 onto the detection face 16 with the magnifying function. This means that an irradiation direction of the illuminating means 14 toward the at least partially specular surface 12 and a main viewing direction of the sensing unit 18 toward the detection face 16 have an alignment angle in relation to each other. The alignment angle may comprise a value within a range of angles larger than 5° and smaller than 175°, larger than 10° and smaller than 170° or larger than 20° and smaller than 160°. Thus, the irradiation of the at least partially specular surface 12 may be effected in an oblique orientation of the illuminating means 14 in relation to the at least partially specular surface 12, the detection face 16 and/or the sensing unit 18.

In other words, the device 10 may have high sensitivity to local differences in inclination of the at least partially specular surface 12 in that direct reflection of the irradiated pattern, for example a fan beam, results in an reinforcement of a change in inclination on the at least partially specular surface 12. The reinforcement of the change in inclination may be influenced or at least partly determined by, e.g., a distance between the detection face 16 and the sampled at least partially specular surface. A resolution of the sensing unit 18, for example the camera resolution, may be accordingly smaller so as to still be able to map a potential surface defect 34 having a possibly very small extension along a direction of the relative motion 28.

Alternatively or additionally, a detailed analysis of the at least partially specular surface 12 may be enabled by the reinforcement of the change in inclination and/or of the angle α in that surface defects 34 which so far have been impossible or hardly possible to sense due to limited camera resolutions, for example on account of insufficient changes in inclination at the surface defect 34, become detectable, i.e. visible, for the camera resolution due to the magnification.

In other words, the evaluation of the light distribution on the detection plane in terms of slow-frequency brightness profiles for evaluating lateral defect structures of particularly small extensions having extensions smaller than the light line width can be effected on the object by exploiting the magnification function.

The pattern which impinges, is reflected by the at least partially specular surface 12 to be sensed and is deformed or shifted by a possible surface defect 34 or other shape defects, for example a light line of a light fan beam, which shows as a more or less deformed pattern on the detection face 16, can be sensed by the sensing unit 18 and be determined via the evaluating means 26, for example a measuring computer.

The detected at least partially specular surface 12 can be analyzed in terms of local changes in the slope of surface defects. Wth a measurement arrangement calibrated accordingly it may also be possible to integrate a measured surface slope so as to partly or entirely reconstruct a global height profile of the at least partially specular surface 12. Thus, partial or absolute 3D shape measurement of the at least partially specular surface 12 can be enabled. For example, a radial and/or lateral runout of a glossy motor vehicle rim can be measured.

In order to perform 3-dimensional measurement of the at least partially specular surface, an alloy wheel may be subjected to a rotational movement, for example, while the illuminating means, or light source, the sensing unit 18 (camera) and the detection face remain at rest. The rotational movement may be caused by a quasi-natural rotation of the wheel about its geometric central axis. Alternatively, it is also possible for the object (alloy wheel) to remain at rest and for the metrological components to be moved in relation thereto.

It may be advantageous for embodiments to generate further information from the camera picture. For example, a defect having a very small lateral extension may be characterized by slight deformation of a light intensity distribution on the detection face, for example in the form of a characteristic depression in the light distribution along a length profile by the line pattern or by an asymmetrical deformation of the light distribution.

Alternatively, it is also feasible for the pattern projected onto the detection face to be evaluated in a staff-supported manner. It is feasible, for example, that a fan beam which is projected onto the detection face via the at least partially specular surface and is projected as a line on the detection face undergoes, when a sufficiently large magnification is set as is described in FIGS. 1a and 1b, a deflection that is possibly clearly discernable for the human eye, for example a deformation or curvature in the case of a surface defect, and that said deformation can be ascertained by the examiner. Possibly, plane surfaces, for example at least partially specular surfaces, can thus be checked for surface defects such as dents, so that a shift of the pattern enables a conclusion to be drawn in terms of the surface defect.

Figure 2:
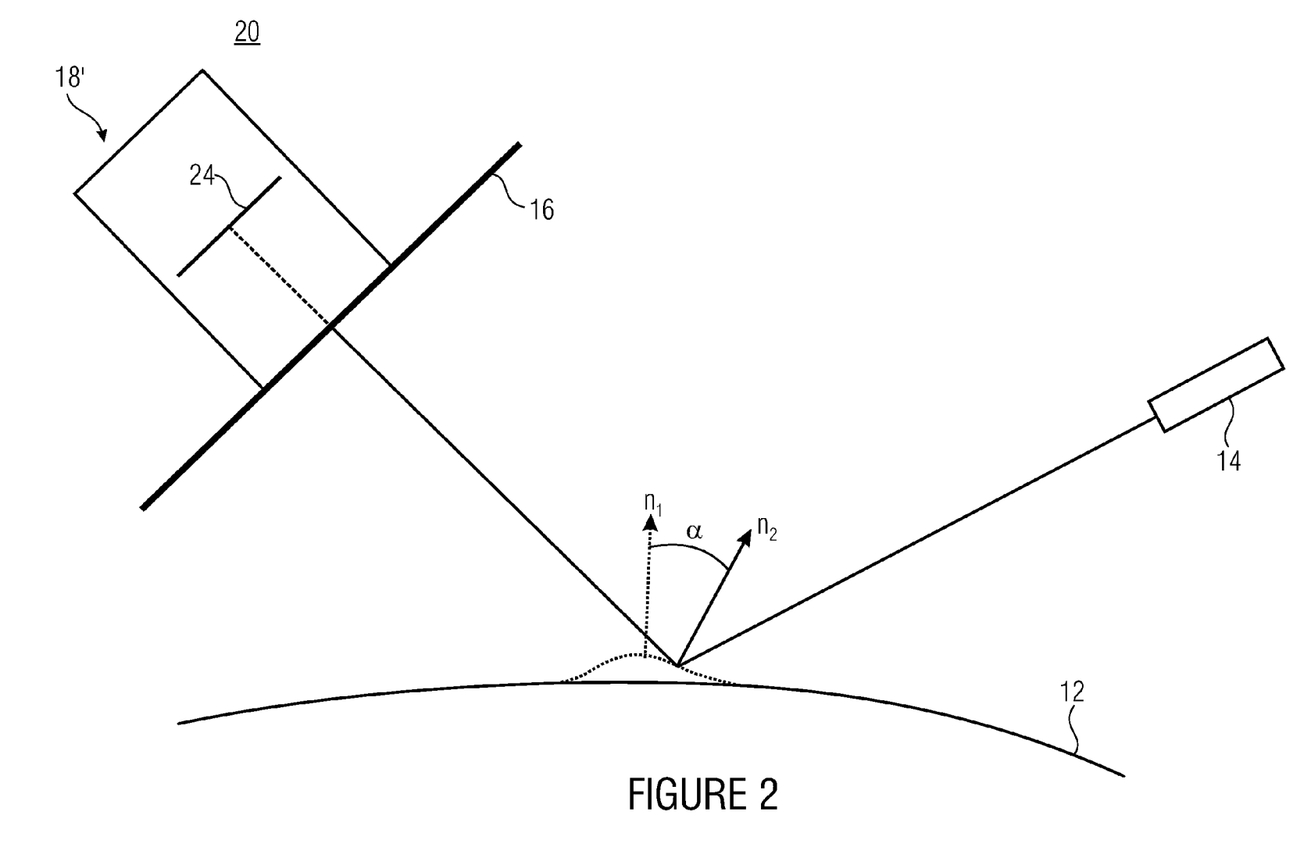
FIG. 2 shows a device for sensing at least partially specular surfaces, in which device the detection plane is coupled to a sensing unit.

FIG. 2 shows a device 20 for sensing at least partially specular surfaces 12, in which device 20 the detection plane 16 is coupled to a sensing unit 18', for example an area scan camera, so that utilization of additional imaging optics may be dispensed with. The detection plane 16 may be optically coupled to the sensing unit 18' by means of a glass fiber taper. The detection face 16 may be configured to be at least partially transparent, so that the pattern projected onto the detection face 16 can be sensed from a side of the detection face 16 which faces away from the at least partially specular surface 12. The optical coupling between the detection face 16 and the sensing unit 18' enables sensing of the pattern through the detection face 16, which means that it is possible to sense the pattern also from a side of the detection face 16 which faces away from the at least partially specular surface 12.

Such an entirely or partly invariable arrangement between the sensing unit 18 and the detection face 16 enables fixed coupling of the detection plane 16 to the sensing unit 18', i.e. at an approximately constant distance, so that imaging optics and/or variable focusing as are shown in FIGS. 1a and 1b may be dispensed with. This may result in reduced mechanical expenditure and may possibly be less costly.

Alternative embodiments show measurement arrangements where the detection face 16 is coupled to the sensing unit 18 via a glass fiber taper, so that imaging optics as are represented, e.g., in FIGS. 1a and 1b, may be dispensed with. An input face of the glass fiber taper may be coupled to the detection face 16.

Alternative embodiments show measurement arrangements where the detection face 16 is an active face of the camera chip 24 and/or of a camera circuit or of a TFT flat panel detector. Utilizing a TFT flat panel detector enables using comparatively large detection faces 16.

Figure 3:
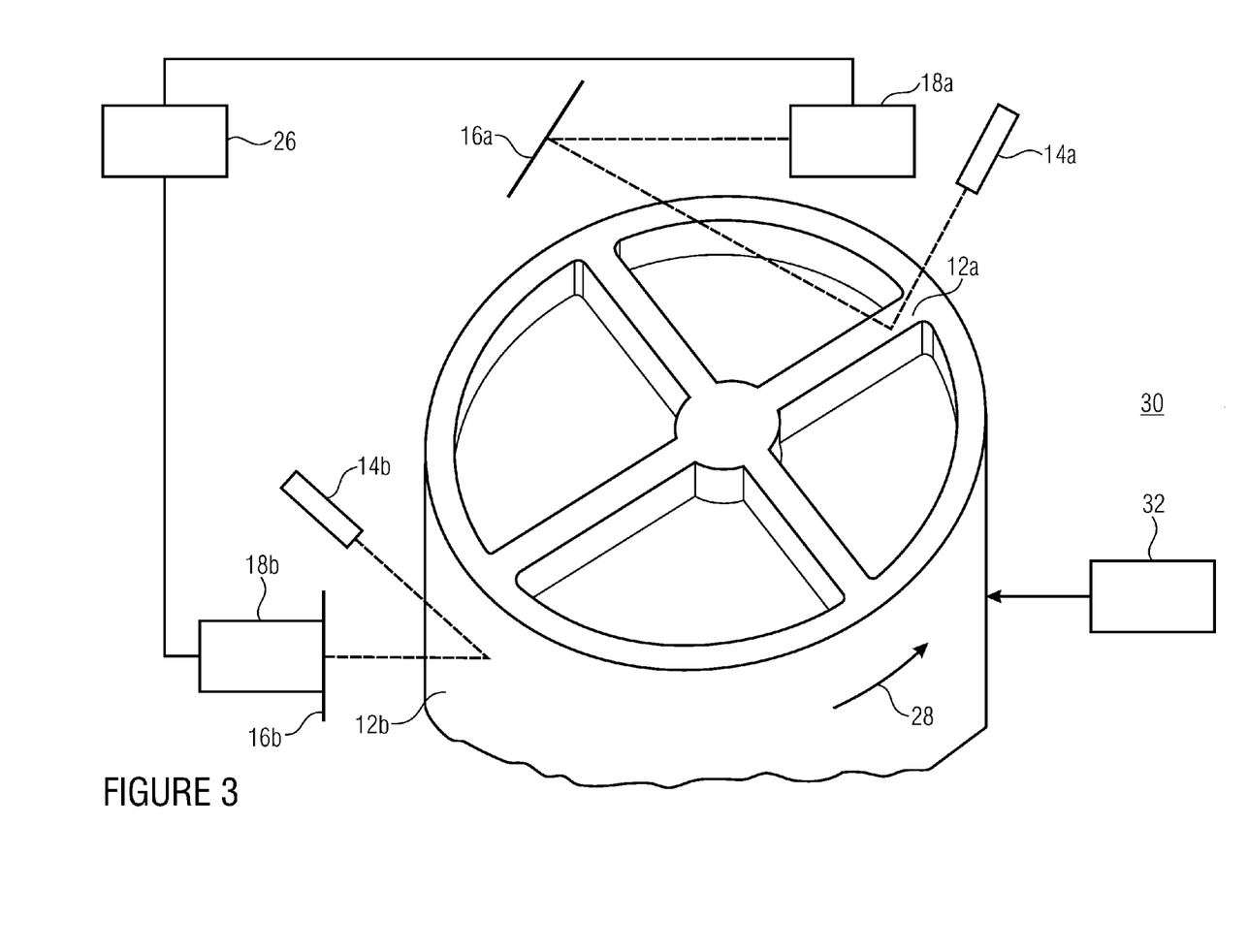
FIG. 3 shows a schematic representation of a measurement system comprising two devices for sensing at least partially specular surfaces.

FIG. 3 shows a schematic representation of a measurement system 30. The measurement system 30 is configured to sense an alloy rim having an at least partially specular surface 12a and an at least partially specular surface 12b. An illuminating means 14a, a detection face 16a and a sensing unit 18a are arranged to sense the at least partially specular surface 12a, as is shown in FIGS. 1a and 1b. An illuminating means 14b, a detection face 16b and a sensing unit 18b are arranged to sense the at least partially specular surface 12b, as is shown in FIG. 2. The sensing units 18a and 18b are connected to the evaluating means 26 configured to produce, on the basis of the information provided by the sensing units 18a and 18b, an at least partially three-dimensional image or model of the alloy rim to be checked for surface defects. The measurement system 30 includes two devices for sensing one of at least partially specular surfaces 12a and 12b, respectively.

By combining several metrological arrangements, i.e. measurement arrangements, at one object, different surface areas 12a and/or 12b can be sensed in a targeted manner. For example, a measurement arrangement 14a, 16a and 18a may be used for sensing the outside, i.e. a top surface 12a of the approximated cylinder of the alloy wheel. The second measurement arrangement 14b, 16b and 18b may be used for sensing a tread 12b, i.e. for a quasi-cylindrical or cone-shaped exterior of a rim. A third measurement arrangement may optionally be used for sensing flanks of the radially extending spokes. Further measurement arrangements may be used for further surface areas to be sensed, for example an interior of the alloy rim. Data of the measurement arrangements (14a, 16a, 18a) and (14b, 16b, 18b) as well as all further measurement arrangements may be evaluated by one or more evaluating units 26.

In addition, for specific inspection tasks such as the inspection of a surface profile of a scattering or diffusely reflecting surface of the rim, measurement arrangements for other test procedures such as a laser light-slit measuring method, for example, may be arranged and may be evaluated in a further evaluating unit or a shared evaluating unit. The one or more evaluating units 26 may comprise interfaces so that measurement data of different measurement arrangements and/or measuring methods may be evaluated in a combined manner.

By means of a high available, i.e. feasible and/or evaluable, measuring frequency of corresponding measuring cameras, the entire object can be sensed within a comparatively short amount of time, for example within one or few seconds, at a high lateral sampling rate, such as within the range of tenths of millimeters, whereby relatively small surface irregularities or other surface defects may be detectable and/or slight or very slight shape deviations may be measurable. Which part of the surface 12a and/or 12b to be sensed that can be sensed in each case may be dependent on the geometric selection of the irradiation direction of one or several measuring means.

In other words, by means of the embodiment described a specific part of the respective surface 12a or 12b, which surface 12a or 12b is irradiated by the respective pattern and from which the respectively specularly reflected intensity is projected onto the detection plane 16a or 16b, can be sensed.

The alloy wheel can be sensed partly, to the greatest possible extent, or fully from different directions by the existing measurement arrangements (14a, 16a, 18a) and (14b, 16b, 18b), wherein the geometry of the measurement arrangements (14a, 16a, 18a) and (14b, 16b, 18b) can remain constant during the relative motion 28. The relative motion 28 may be a rotation moving the alloy wheel in relation to all of the measurement arrangements, for example. Alternatively, the alloy wheel may remain at rest, and the measurement arrangements (14a, 16a, 18a) and (14b, 16b, 18b) may be moved individually or together in relation to the alloy wheel at the relative speed 28.

For example, in order to achieve optimum pictures, i.e. a high defect recognition rate, for different types of allow wheels, for example all of or only specific metrological components of the individual measurement arrangements (14a, 16a, 18a) and/or (14b, 16b, 18b) may be specifically positioned in accordance with different wheel geometries by additional motorized movement units. This may be effected either by translational and/or by rotational positioning units. For example, a shape of spokes, such as angular, round, oval or having a variable diameter, may be taken into account such that the measuring means (14a, 16a, 18a) is moved such that different spoke geometries can be sensed. Alternatively or additionally, different types of different alloy wheels having different widths may be sensed in that the measuring means 14b, 16b, 18b is moved such that an enlarged at least partially specular surface 12b continues to be fully sensed. Alternatively or additionally, both a respective measurement arrangement (14a, 16a, 18a) and/or (14b, 16b, 18b) and a measurement system 30 may include several illuminating means 14a and 14b so as to at least partly sense a same at least partially specular surface 12a or 12b since possibly different types of surface defects enable a higher recognition rate of the respective type of surface defect when viewed from different illumination angles. For example, a first illuminating means may be arranged at an angle of 15°, and a second illuminating means may be arranged at an angle of 30°, in relation to the at least partially specular surface 12b. Different illuminating means 14a and/or 14b arranged at different angles in relation to an at least partially specular surface 12a or 12b may be switched on selectively to perform, e.g., examination in terms of one type of surface defects. For example, during a first revolution of a wheel rim, a first illuminating means 14a or 14b may project a first pattern, and during a second revolution, a second illuminating means 14b or 14a may project a same or different pattern.

Alternatively or additionally, it is feasible for two or more illuminating means 14a and/or 14b to be arranged at different angles in relation to an at least partially specular surface 12a or 12b and to each project a pattern, respectively, onto different detection faces 16a and 16b or onto different areas of a shared detection face 16a or 16b.

Alternatively or additionally, the measurement system 30 may include only one or may include several devices in accordance with the preceding embodiments, which devices may be moved or may remain at rest, independently of one another, in relation to an object to be tested, or wherein a relative motion can be set by moving the object to be tested or the measurement arrangement.

Figure 4:
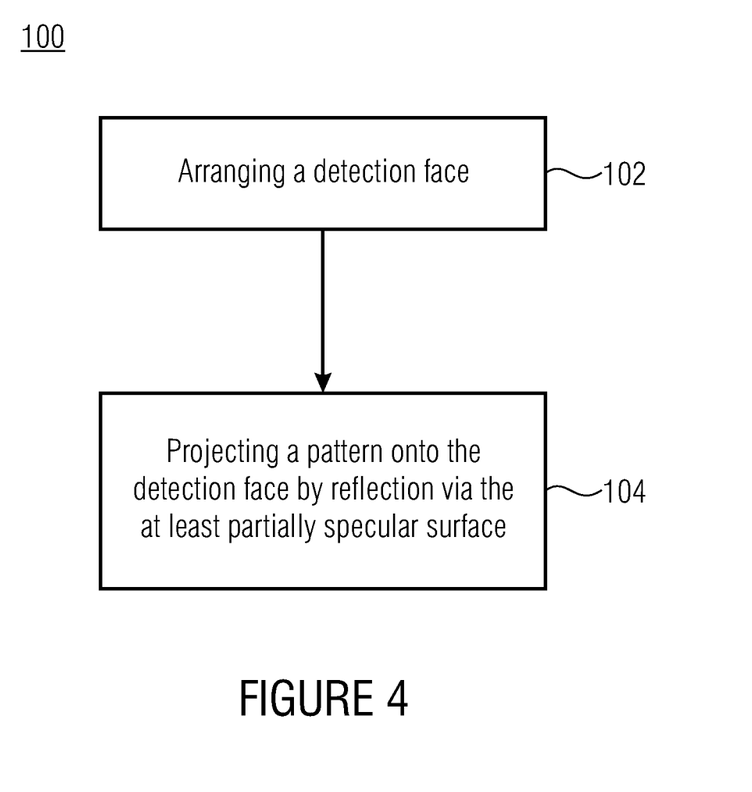
FIG. 4 shows a block diagram of a method of sensing at least partially specular surfaces.

FIG. 4 shows a block diagram of a method 100 of sensing at least partially specular surfaces. A first step 102 comprises arranging a detection face. A second step 104 comprises projecting a pattern onto the detection face by reflection via the at least partially specular surface.

By using a detection plane, a surface that is partially, predominantly or fully reflecting in a specular, i.e. mirroring, manner can be sensed. The method 100 described here might be referred to as an "inverse deflectometry" or by words to that effect: "inverse" since the light of the pattern takes a path that is inverse to deflectometry. The light can be reflected by an e.g. point-shaped light source onto a two-dimensional detection screen via the at least partially specular surface to be sensed; "deflectometry" since the pattern is first of all deflected via a reflection at the at least partially specular surface and is subsequently projected, i.e. collected, on the detection face, whereby a high, i.e. intense, potential sensitivity to local surface inclinations at the at least partially specular surface may be adjustable for the method 100. If a light radiation distribution that is formed in a fan-like manner is used for the method 100, then the method may also be referred to as an "inverse light-slit deflectometry" or by words to that effect: "light-slit" since a light-slit camera may be employed for evaluating the light distribution of the pattern (e.g. of the light fan) on the detection face.

Reflecting or partially reflecting surfaces may be automatically sensed and/or measured and/or checked for possible surface defects during a movement. While using an optical measurement setup comprising a sensing means such as an area scan camera, a suitable illuminating means, the at least partially specular surface to be sensed and an evaluating unit that is computer-supported, for example, examination of the at least partially specular surface can automatically for surface defects can be performed automatically. The area scan camera may be configured, e.g., to produce a brightness picture of a detection plane.

With a suitable selection of the measurement arrangement between light source, surface, detection plane and/or sensing unit, very small local differences in inclination of the surface normal may already be detectable which cannot be detected or can only be detected insufficiently by means of triangulation measuring methods, for example. Deflectometric methods may sometimes sense said surface defects merely by using a long test duration.

The method 100 may be combined with light-slit deflectometry. In many cases, an object to be tested exhibits a combination of surfaces with specular and/or diffuse reflection, it being possible for the proportion of the two reflection proportions to be dependent on the illumination angle. For example, the proportion of specular reflection may increase as the level of shallowness of the incidence of light of the pattern increases. This is particularly true for clear-lacquered surfaces of alloy rims, it being possible for various types of defects to show in the diffusely and specularly reflected intensity. In a combination of measuring methods, combined utilization of light sources and/or illuminating means may be possible.

As compared to deflectometry measuring methods, the method 100 may enable, by using specific measuring cameras, an achievable measuring and evaluating frequency, which is high due to the measuring cameras, on the evaluating unit directly on or after the image sensor (camera chip) and, thus, substantially faster sensing of the surface. This means that what is sensed and transmitted to the evaluating unit, for example, is no complete image in the sense of a photo of the detection plane, but possibly a brightness image that is compressed as compared to the complete image. Alternatively or additionally, so-called piggyback chips or field programmable gate arrays (FPGA) may also be used, for example, to enable data reduction. For example, an FPGA may be directly coupled to the image sensor so as to process and/or compress the picture sensed by the image sensor. A lower data transmission rate from the sensing unit to the evaluating unit enables transmission of several pictures per time unit as well as faster calculation of the results.

The devices and methods described enable contactless sensing of at least partially mirroring or even high-gloss surfaces. One possible application is quality inspection with regard to local surface defects such as dents, bumps, scratches, grooves and/or for measuring the surface or the entire body. With motor-vehicle alloy rims, lacquer defects or scratches may occur which manifest as short-range structures with little or very little height extensions. Alternatively or additionally, shape measurement of high-gloss surfaces, for example measurement of the concentricity of specular motor-vehicle rims, can be performed.

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described in connection with or as a method step also represent a description of a corresponding block or detail or feature of a corresponding device.

Depending on specific implementation requirements, embodiments of the invention may be implemented in hardware or in software. Implementation may be effected while using a digital storage medium, for example a floppy disc, a DVD, a Blu-ray disc, a CD, a ROM, a PROM, an EPROM, an EEPROM or a FLASH memory, a hard disc or any other magnetic or optical memory which has electronically readable control signals stored thereon which may cooperate, or cooperate, with a programmable computer system such that the respective method is performed. This is why the digital storage medium may be computer-readable. Some embodiments in accordance with the invention thus include a data carrier which comprises electronically readable control signals that are capable of cooperating with a programmable computer system such that any of the methods described herein is performed.

Generally, embodiments of the present invention may be implemented as a computer program product having a program code, the program code being effective to perform any of the methods when the computer program product runs on a computer. The program code may also be stored on a machine-readable carrier, for example.

Other embodiments include the computer program for performing any of the methods described herein, said computer program being stored on a machine-readable carrier.

In other words, an embodiment of the inventive method thus is a computer program which has a program code for performing any of the methods described herein, when the computer program runs on a computer. A further embodiment of the inventive methods thus is a data carrier (or a digital storage medium or a computer-readable medium) on which the computer program for performing any of the methods described herein is recorded.

A further embodiment of the inventive method thus includes a data stream or a sequence of signals representing the computer program for performing any of the methods described herein. The data stream or the sequence of signals may be configured, for example, to be transferred via a data communication link, for example via the internet.

A further embodiment includes a processing means, for example a computer or a programmable logic device, configured or adapted to perform any of the methods described herein.

A further embodiment includes a computer on which the computer program for performing any of the methods described herein is installed.

In some embodiments, a programmable logic device (for example a field-programmable gate array, an FPGA) may be used for performing some or all of the functionalities of the methods described herein. In some embodiments, a field-programmable gate array may cooperate with a microprocessor to perform any of the methods described herein. Generally, the methods are performed, in some embodiments, by any hardware device. Said hardware device may be any universally applicable hardware such as a computer processor (CPU), or may be a hardware specific to the method, such as an ASIC.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A device for sensing at least partially specular surfaces, comprising:
    a detection face;
    illuminator configured to project a pattern onto the detection face by reflection via the at least partially specular surface; and
    a sensing unit configured to sense the pattern projected onto the detection face and to evaluate an image, which has been sensed from the detection face, in a column-by-column manner in terms of a global or local intensity maximum;
    the illuminator comprising a line projector configured to emit a line pattern, the line pattern being a light fan beam.

2. The device as claimed in claim 1, wherein the sensing unit is configured to sense the pattern, which is projected onto the detection face, during a continuous relative motion between the illuminator and the detection face or the at least partially specular surface and the detection face.

3. The device as claimed in claim 2, wherein the local evaluating unit is configured to perform defect detection on the basis of the pattern captured by the image sensor.

4. The device as claimed in claim 1, wherein the detection face is configured to generate a real image of the pattern.

5. The device as claimed in claim 4, wherein the sensing unit is configured to map the pattern, which is projected onto the detection face and is scattered by the detection face, onto an image sensor.

6. The device as claimed in claim 4, wherein the pattern is a line pattern.

7. The device as claimed in claim 6, wherein the local evaluating unit along with the image sensor is arranged within a housing and is configured to output a recognized line pattern at a data rate smaller than 10% of a data rate of a picture captured by the image sensor.

8. The device as claimed in claim 4, wherein the sensing unit is configured to sense the pattern, which is scattered by the detection face, in transmission or reflection.

9. The device as claimed in claim 1, wherein the sensing unit comprises a camera.

10. The device as claimed in claim 1, wherein the sensing unit comprises a light-slit camera.

11. The device as claimed in claim 1, wherein the sensing unit comprises an area scan camera.

12. The device as claimed in claim 1, further comprising a positioning unit configured to perform a relative motion between the illuminator and the detection face or the at least partially specular surface and the detection face.

13. The device as claimed in claim 1, wherein the illuminator comprises a laser line projector configured to emit a line pattern.

14. The device as claimed in claim 1, wherein the illuminator is configured to emit ultraviolet radiation or extreme ultraviolet radiation.

15. The device as claimed in claim 1, wherein the detection face is optically coupled to the sensing unit by a tapered glass fiber.

16. The device as claimed in claim 1, wherein the illuminator is configured to take into account, during projection of the pattern onto the detection face, a variable distance between the illuminator and the at least partially specular surface and to focus on the detection face.

17. The device as claimed in claim 1, wherein the detection face is configured to shift ultraviolet or extreme ultraviolet measuring light to a visible spectrum.

18. The device as claimed in claim 1, wherein the detection face is an active face of the image sensor and wherein no imaging optics are arranged between the at least partially specular surface and the image sensor.

19. The device as claimed in claim 1, configured to measure at least a wheel rim.

20. A method of sensing at least partially specular surfaces, comprising:
    arranging a detection face;
    projecting, by means of an illuminator, a pattern onto the detection face by reflection via the at least partially specular surface;
    sensing the pattern projected onto the detection face;
    evaluating an image, which has been sensed by the detection face, with regard to a global or local intensity maximum in a column-by-column manner;
    said projecting being implemented such that a line pattern that is a light fan beam is emitted.

21. The method as claimed in claim 20, comprising:
    performing a continuous relative motion between the illuminator and the detection face or the at least partially specular surface and the detection face, while the pattern projected onto the detection face is being sensed.

22. A non-transitory digital storage medium having a computer program stored thereon to perform the method according to claim 20 when said computer program is run by a computer.

* * * * *